(12) United States Patent
Maslowski et al.

(10) Patent No.: US 9,902,937 B2
(45) Date of Patent: *Feb. 27, 2018

(54) METHODS FOR CULTURING MINIMALLY-PASSAGED FIBROBLASTS AND USES THEREOF

(71) Applicant: Fibrocell Technologies, Inc., Exton, PA (US)

(72) Inventors: John Maslowski, Pottstown, PA (US); Myrna F. Thomas, Hainesport, NJ (US); Marie A. Lindner, Radnor, PA (US)

(73) Assignee: Fibrocell Technologies, Inc., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/280,957

(22) Filed: May 19, 2014

(65) Prior Publication Data

US 2014/0335057 A1 Nov. 13, 2014

Related U.S. Application Data

(63) Continuation of application No. 12/438,932, filed as application No. PCT/US2007/077141 on Aug. 29, 2007, now Pat. No. 8,728,819.

(60) Provisional application No. 60/823,871, filed on Aug. 29, 2006.

(51) Int. Cl.
*A01N 63/00* (2006.01)
*C12N 5/077* (2010.01)

(52) U.S. Cl.
CPC ........ *C12N 5/0656* (2013.01); *C12N 2509/00* (2013.01)

(58) Field of Classification Search
None
See application file for complete search history.

(56) References Cited

U.S. PATENT DOCUMENTS

| | | | |
|---|---|---|---|
| 4,524,065 | A | 6/1985 | Pinnell |
| 4,772,557 | A | 9/1988 | Elsen |
| 5,135,913 | A | 8/1992 | Pickart |
| 5,372,494 | A | 12/1994 | Vaughan |
| 5,660,850 | A | 8/1997 | Boss, Jr. |
| 5,935,847 | A | 8/1999 | Smith et al. |
| 6,042,841 | A | 3/2000 | Alaluf et al. |
| 6,110,459 | A | 8/2000 | Mickle |
| 6,733,530 | B1 | 5/2004 | Lam |
| 7,115,274 | B2 | 10/2006 | Keller |
| 7,767,452 | B2 | 8/2010 | Kleinsek |
| 7,799,325 | B2 | 9/2010 | Kleinsek |
| 2008/0152628 | A1 | 6/2008 | Kleinsek |
| 2009/0123503 | A1 | 5/2009 | Naughton et al. |
| 2009/0239254 | A1 | 9/2009 | Duval et al. |
| 2011/0110898 | A1 | 5/2011 | Kleinsek |
| 2012/0219634 | A1 | 8/2012 | Maslowski et al. |

FOREIGN PATENT DOCUMENTS

| | | |
|---|---|---|
| JP | 2004339107 A | 12/2004 |
| WO | 02098365 A2 | 12/2002 |
| WO | 03097837 A1 | 11/2003 |
| WO | 2006125991 A1 | 11/2006 |
| WO | 2008027984 A1 | 3/2008 |
| WO | 2009121761 A1 | 10/2009 |
| WO | 2011/098391 | 8/2011 |
| WO | 2012027742 A2 | 3/2012 |

OTHER PUBLICATIONS

Hager et al., J Invest Dermatol, 1999, vol. 112, No. 6, p. 971-976.*
EUSTAR, Distiler, Apr. 2006, p. 1-16.*
Randolph et al., A. J Invest Dermatol, 1998, vol. 111, p. 478-484.*
EuroBioBank (INNCB-Marina Mora, 1st. Nazionale Neurologico Carlo Besta, Laboratory Procedures for Human Cell Culture 2005, p. 1-4.*
Ghahary, et al., "Collagenase production is lower in post-burn hypertrophic scar ibroblasts than in normal fibroblasts and is reduced by insulin-like growth factor-1", J. Invest Dermal., 106(3):46-81 (1996).
Watson, et al., "Autologous fibroblasts for treatment of facial rhytids and dermal depressions. A pilot study", Arch. Facial Plast. Surg., 1:165-70 (1999).
NPL search results (Sep. 9, 2013).
EUSTAR Guidelines, 2006, Distler, et al., "Protocol for culture of dermal fibroblast derived enzymatic digestion".
Lyons et al., The Journal of Cell Biology, 1988, vol. 106, p. 1659-1665.
Fisher Scientific Biotechnology catalogue, 1995, Cover and p. 248.
Isayeva et al., BioProcessing Journal, Sep. 2003, p. 75-81.
"Liberase Purified Collagenase Blends for Tissue Dissociation", Biochem.ica, 2000, No. 2, p. 22-23.
Bryne, Generation of isogenic pluripotent stem cells, Hum Mol Gen 2008 17:R37-R41.
Byrne et al., Producing primate embryonic stem cells by somatic cell nuclear transfer, Nature 2007 450(7169):497-502.
Carruthers et al., A validated facial grading scale: the future of facial ageing measurements tools?, Journal of Cosmetic and Laser Therapy 2010 12:235-241.
Cowan et al., Nuclear reprogramming of somatic cells after fusion with human embryonic stem cells, Science 2005 309 (5739)1369-73.
Database accession No. 1381185E, Essential Serum, 2 pages, Published May 2010, accessed Mar. 5, 2011.
Fantasia et al., Differential levels of elastin fibers and TGF-beta signaling in the skin of caucasians and african americans, J Dermatol Sci 2013 70:159-165.

(Continued)

*Primary Examiner* — Kade Ariani
(74) *Attorney, Agent, or Firm* — Stradley Ronon Stevens & Young, LLP

(57) ABSTRACT

The present invention relates to novel methods of growing at least 100 million minimally-passaged fibroblasts from a small biopsy specimen. The invention includes methods wherein a small biopsy specimen is seeded directly into a large tissue culture flask, and passaged no more than three times.

8 Claims, No Drawings

(56) References Cited

OTHER PUBLICATIONS

Federal Register, vol. 79, No. 241, Tuesday Dec. 16, 2014, pp. 74618-74633, accessed from http://www.gpo.gov/fdsys/pkg/FR-2014-12-16/pdf/2014-29414.pdf on Dec. 16, 2014.
Fisher et al., Mechanisms of photoaging and chronological skin aging, Arch Dermatol 2002 138(11):1462-70.
Grimes, Skin and hair cosmetic issues in women of color, Dermatologic Clinics 2000 18(4):659-65.
Guidance memorandum Mar. 4, 2014 accessed Mar. 27, 2014 from http://www.uspto.gov/patents/law/exam/myriad-mayo_guidiance.pdf.
Hochedlinger et al., Epigenetic reprogramming and induced pluripotency, Development 2009 136(4):509-23.
Kanawaty et al., Genomic analysis of induced pluripotent stem (iPS) cells: routes to reprogramming, Bioessays 2009 31(2):134-8.
Kindred et al., Overview of the structure and function of ethnic skin, Nutritional Cosmetics: Beauty from within, Tabor and Blair (eds), Willim Andrew Inc. pp. 47-69 2009.
MacIntyre et al., Characterisation of human embryonic stem cells conditioning media by 1H-nuclear magentic resonance spectroscopy, Plos One 2011 6(2):e16732.
Mehta et al., Reduction in facial phtodamage by a topical growth factor product, J Drugs Dermatol 2008 7(9):864-71, Abstract Only.
Mintel, Essential Serum, downloaded from http://www.gnpd.com, accessed May 2010.
Montagna and Carlisle, The architecture of black and white facial skin, J Am Acad Dermatol 1991 24:929-37.
NPL document mdc_examples_nature-based_products accessed from http://www.uspto.gov/patents/law/exam/mdc_examples_nature-based_products.pdf on Dec. 16, 2014.
Office Action dated Jan. 28, 2016 in related U.S. Appl. No. 13/785,219.
Official Action dated Feb. 22, 2015 from U.S. Appl. No. 13/220,163.
Rawlings, Ethnic skin types: are there differences in skin structure and function, Int J Cosmetic Sci 2006 28:79-93.
Richards et al., Structure and function of ethnic skin and hair, Dermatol Clin 2003 21:595-600.
Rosdahl and Szabo, Thymidine labelling of epidermal melanocytoes in UV-irradiated skin, Acta Dermatovenereologica 56(2):159-61.
Son et al., Topical application of 17beta-estradiol increases extracellular matrix protein synthesis by stimulating TGF-beta. signaling in aged human skin in vivo, J Invest Dermatol 2005 124:1149-1161.
Sparman et al., Epigenetic reprogramming by somatic cell nuclear transfer in primates, Stem Cells 2009 27 (6):1255-64.
Takahashi et al., Induction of pluripotent stem cells from adult human flibroblasts by defined factors, Cell 2007 31 (5):861-72.
Taylor, Skin of color: biology, structure, function, and implications for dermatologic disease, J Am Acad Dermatol 2002 46(2 Suppl Understanding):S41-62.
thefreedictionary.com. Allograft. Definition retrieved from the world wide web on Mar. 25, 2014. <http://www.thefreedictionary.com/allograft>.
Dawson, The significance of endotoxin to cell culture and biotechnology, 1998, LAL Update, vol. 16, No. 1, available at http://www.acciusa.com/pdfs/newsletter/updt0398.pdf, accessed Jul. 15, 2016.
EMEA by the European Medicines Agency, "Quality of Biotechnological Products: Derivation and Characterisation of Cell Substrates Used for Production of Biotechnological/Biological Products", http://www.ema.europa.eu/docs/en_GB/document_library/Scientific_guideline/2009/091WC500003280.pdf, online since Mar. 15, 1998.
Final Office Action dated Jul. 21, 2016 in U.S. Appl. No. 14/100,871.
Human Pathogens, accessed from the CDC at https://www.cdc.gov/biosafety/piblications/bmb15/bmbl5_appendixh.pdf on Jul. 15, 2016, online since Feb. 16, 2007.
Official Action dated Apr. 5, 2017 from related U.S. Appl. No. 13/785,219.
Office Action dated Jul. 13, 2017 in related U.S. Appl. No. 14/100,871.
West, T., et al., "Autologous Human Collagen and Dermal Fibroblasts for Soft Tissue Augmentation", Dermatologic Surgery, 1998, vol. 24, p. 510-512.

* cited by examiner

METHODS FOR CULTURING MINIMALLY-PASSAGED FIBROBLASTS AND USES THEREOF

FIELD OF THE INVENTION

The present invention, relates to novel methods of culturing and growing autologous fibroblasts, and methods of use thereof to promote healing and regeneration of tissue in an animal.

Fibroblasts are connective-tissue cells involved in tissue repair. Fibroblasts synthesize a variety of compounds, including collagens, glycosaminoglycans, reticular and elastic fibers, and glycoproteins found in the extracellular matrix. When a tissue is injured, nearby fibroblasts migrate into the wound, proliferate, and produce large amounts of collagenous matrix, which helps to isolate and repair the damaged tissue. See, e.g., Alberts et al., Molecular Biology of the Cell p. 987, 2nd ed., (1992).

Co-owned U.S. Pat. Nos. 5,591,444; 5,858,390; 5,660,850; 5,663,372; 6,432,710; and 6,878,383 (incorporated herein by reference in their entirety), broadly describe the repair of skin, bone, and other tissues prior to the advent of the growing of fibroblast cultures drawn from biopsies of patients in need of tissue repair to effect such repair. In general, these patents also disclose compositions and methods of growing and culturing passaged autologous fibroblasts and using such fibroblasts to repair skin, bone, and other tissues.

Fibroblasts take significant time to grow to sufficient numbers, and the passaging of cell cultures required to generate such numbers yields fibroblasts which may suffer from decreased viability and effectiveness. Multiply passaging fibroblasts also suffers drawbacks from increased use of materials, increased cost, and increased opportunities for contamination of the cultures. Yet the art has not been able to generate such fibroblasts in sufficient numbers and effectiveness without a multiplicity of passages. The art, therefore, is in need of simplified methods to generate such fibroblasts without the shortcomings of multiple passages. The present invention provides such a simplified method of growing such fibroblasts.

SUMMARY OF THE INVENTION

In a surprising discovery, the inventors herein have found that a small 1-5 mm full thickness biopsy (on the order of a 3×3 mm circular shape) from a subject may be digested with a disassociating or digestive enzyme, such as a collagenase enzyme (e.g., liberase) or trypsin to free dermal fibroblasts, which may be directly seeded into larger culture flasks (in comparison to the typical known explant method) with an appropriate growth medium. The fibroblasts grow to confluence in large numbers after a short time of between about one and three weeks. A passage to a larger flask, or an even larger multilayer culture stack, such as a 5- or 10-layer stack, with growth medium and routine addition of supplementary medium, leads to a harvest of autologous fibroblasts on the order of $3\times10^8$ or more cells. The cells may then be shipped directly to the point of treatment location, either fresh or cryopreserved, or may be cryopreserved, stored, and shipped at a later date.

Alternatively, the cells may be further cultured in additional multilayer culture stacks to generate larger quantities of cells, where desired. For example, the $3\times10^8$ or more cells in a 10-layer stack may be split into four additional 10-layer stacks, and cultured according to the invention to generation more than $1\times10^9$ cells.

The resulting fibroblasts grown by this method, which have been minimally passaged, have improved viability and effectiveness compared with prior methods of preparing cultured autologous fibroblasts.

In general, the method of the invention comprises obtaining a sufficient number of autologous fibroblasts for treatment (at least 100 million cells) by minimal passaging from a small biopsy specimen. The cells obtained may then be used for repair of dermal defects by administering the autologous fibroblasts to a defect in skin, bone, or other tissue. The fibroblasts are prepared as a pharmaceutical composition as described below, for direct injection, or may be delivered by other means such as topically. Preferably, the autologous fibroblasts are obtained from a tissue which is the same type of tissue as the defect to be repaired. Additionally, the autologous fibroblasts may be cultured in the animal's own serum, or m fetal bovine serum. The fibroblasts are preferably passaged in culture at most three times, more preferably only one or two times. Between about 10 and 20 million autologous fibroblasts are generally administered per treatment.

The invention further provides a method of rendering the minimally passaged dermal fibroblasts substantially free of immunogenic proteins present in the culture medium where desirable. The method comprises incubating the expanded fibroblasts for a period of time in reduced-serum medium or serum-free medium supplemented with other nutrients.

The present invention further provides methods of correcting defects in an animal, such as a mammal, particularly a human. Desirably, the defect to be corrected is susceptible to healing upon administration of autologous fibroblasts, such as defects in skin, bone, or other connective tissue.

The present invention provides methods of generating such minimally passaged fibroblasts, and formulating a pharmaceutical composition for the repair, augmentation, or regeneration of tissue, without surgery, wherein the composition is histocompatible with a subject, thereby avoiding elicitation of an immune response and inflammation in the tissues of the subject near the site of degeneration of tissue.

In one aspect, the present invention uses gentamicin as an antibacterial agent, as well as amphotericin B as a fungicide, during the culture stage. In another aspect, the invention avoids the use of antibiotics in the subject, and hence prevents the emergence of antibiotic resistant pathogens and deleterious side effects associated with antibiotics in the subject. In another aspect, the invention includes passaged autologous fibroblasts that can withstand resorption so that subsequent injections are not needed, and to prevent the elicitation of an immune response in the subject.

In one aspect, the present invention provides a method of correcting cosmetic and aesthetic defects in the skin of a subject by the injection of a suspension of autologous dermal fibroblasts into the dermis and subcutaneous tissue subadjacent to the defect. Typical defects that can be corrected by this method include rhytids, stretch marks, depressed scars, cutaneous depressions of non-traumatic origin, scaring from acne vulgaris, and hypoplasia of the lip. Other tissues may also be repaired, such as vocal cords, oral mucosa, the gingival mucosa, or the palatal mucosa or skin, which has degenerated as a result of a disease or disorder such as periodontal disease, trauma, dermatoses, recurrent aphthous stomatitis, and infections. Additionally, other damaged tissue may be repaired using the fibroblasts generated by the method of the invention, such as burns and burn scars.

The cells that are injected are cells that are histocompatible with the subject, that is, they are autologous cells, that have been expanded by minimal passage in a cell culture system initiated by a biopsy specimen.

Thus, in one aspect, the invention is a method of generating at least 100 million minimally-passaged fibroblasts from a small biopsy specimen, comprising the steps of:
 a) digesting the small biopsy specimen with a dissociative or digestive enzyme to form a cell suspension;
 b) seeding the cell suspension into a first large tissue culture flask;
 c) culturing a fibroblast cell population in the first large tissue culture flask through no more than three passages into sequentially larger tissue culture flasks; and
 d) harvesting the minimally-passaged fibroblasts.

In one aspect, the enzyme is trypsin, while in another, the enzyme is a collagenase enzyme. The collagenase enzyme may be liberase. In another aspect, the minimally-passaged fibroblasts have been passaged no more than two times, or in other aspects, no more than once. In another aspect, the method of the invention generates at least 200 million minimally-passaged fibroblasts are generated. In yet another aspect, the method of the invention generates at least 300 million minimally-passaged fibroblasts are generated.

In another aspect, the first large tissue culture flask is at least the size of a T-125 flask, and preferably is a T-175 or a T-225 flask. The sequentially larger tissue culture flasks may be a T-500 flask or a multilayer cell culture stack, such as a 5- or 10-layer cell culture stack.

In other aspects, the invention provides a method of treating a defect in the skin, bone, or other connective tissue of an animal, comprising the step of administering to the animal the minimally-passaged fibroblasts generated as described above, wherein the biopsy specimen is taken from the animal, i.e., the fibroblasts are autologous fibroblasts.

The defect may be selected from the group consisting of rhytids, stretch marks, depressed scars, cutaneous depressions of non-traumatic origin, scarring from acne vulgaris, hypoplasia of the lip, vocal cords defects, defects of the oral mucosa, the gingival mucosa, or the palatal mucosa or skin, burns, and burn scars.

Administrations may each comprise 10-20 million minimally-passaged autologous fibroblasts, and may be injected into the defect area or area subadjacent to the defect. In another aspect, the invention provides for topical application of the minimally-passaged fibroblasts.

Other objects and advantages will become apparent to those skilled in the art from a review of the ensuing description.

DETAILED DESCRIPTION OF THE INVENTION

The present invention is based on the surprising and unexpected discovery that biopsy derived fibroblasts may be seeded and cultured to numbers sufficient for exogenous administration to a patient to promote healing of tissue without requiring multiple passaging of the cultured cells. In the past, such biopsy-derived fibroblasts were required to be seeded at higher density in smaller tissue culture flasks, then multiply passaged into sequentially larger flasks, in order to generate the desired number of cells. The present invention solves the problem of multiple passaging by providing a method of seeding the biopsy-derived cells directly into larger flasks, followed by only a minimum of passages to achieve the large number of cells needed for treatment of defects in skin, bone, and other connective tissue. As used herein, a "small biopsy" is one whose size is 1-5 mm thick, and between 4 and 12 $cm^2$.

Methods of Generating Large Numbers of Fibroblasts with Minimal Passaging

Initially, a dermal fibroblast culture is initiated from a small 1 to 5 mm full thickness biopsy specimen, generally taken from the skin, gums, or palate of the subject. Because of the phenomenon of allograft rejection, which is well known to transplantation surgeons and immunologists, it is preferable that the cultured fibroblasts be histocompatible with the host. Histocompatibility can be ensured by obtaining a biopsy of the subject to be treated and culturing the fibroblasts from this specimen.

In brief, the method of the invention may be performed as follows: Before the initiation of the culture, the biopsy is washed several times in a wash media comprising IMDM medium with antibiotic agents, such as gentamicin (antibacterial) at a concentration of between 20-40 mg/mL, preferably about 30 mg/mL, and amphotericin B (antifungal) at a concentration of between 10-20 µg/mL, preferably about 15 µg/mL. The biopsy specimen is then digested using a solution of a dissociative or digestive enzyme, and vortexed in an orbital shaker. In one embodiment, the enzyme is trypsin. In another embodiment, the enzyme is a collagenase enzyme, preferably liberase. Growth medium is than added to neutralize the enzyme (when such neutralization is necessary), and the cells are pelleted in a centrifuge. Preferably, growth medium comprises IMDM (containing HEPES and L-glutamine and the aforementioned antibiotics) and 10% fetal bovine serum (FBS), although variations in growth medium will be appreciated by those of skill in the art.

The cells are resuspended in growth, medium, and pipetted into a large tissue culture flask along with sufficient growth medium to keep all cells submerged. A "large" tissue culture flask is one which is at least the size of a T-125 flask, including T-125, T-150, T-175, T-225, T-500, and multilayer culture stacks. The flask is then incubated between 35-39° C. with about 4-6% $CO_2$. Supplementation of the flask with additional pre-warmed growth medium may be performed at intervals as needed, usually about every 3-5 days. "Pre-warmed" medium is medium which has been warmed after removal from refrigeration, though such medium need not be warmed to physiological temperatures. When supplementing with fresh media, it may be desirable to remove about half of the existing media before adding in the fresh media, which may then be stored as conditioned medium for use elsewhere.

When the cells have reached about 40-100% confluence in the flask, they are passaged into a larger tissue culture flask, such as a T-500 flask or multilayer culture stack. This is accomplished by first removing the growth medium, which now comprises a variety of factors secreted from the growing culture (i.e., it is conditioned medium), which may be stored for use later. The flask is washed with phosphate buffered saline (PBS), then a solution of trypsin-EDTA is used to detach the fibroblasts from the wall of the tissue culture flask, according to procedures known in the art. The detached fibroblasts are suspended in fresh growth media to inactive the trypsin and transferred to a larger flask, such as a T-500 flask or multilayer stack. Again, fresh growth medium may be added to the flask as needed.

If the first passage of cells was info a multilayer stack, or has otherwise produced sufficient cells for treatment, the cells are harvested as described below. Otherwise the same passaging procedure is used when the larger flask reaches about 95-100% confluence, to transfer the cells to a yet larger flask, such as a multilayer culture stack. Once again, additional growth medium may be added as needed and conditioned medium may be stored for later use.

When the cells in the multilayer culture stack have reached about 95-100% confluence, they are harvested, generally yielding at least $1.0 \times 10^8$ cells, preferably at least $2.0 \times 10^8$ cells, more preferably at least $3.0 \times 10^8$ cells. The cells may be cryopreserved as detailed below, or may be further cultured in additional multilayer culture stacks to generate larger quantities of cells, where desired. For example, the $3 \times 10^8$ or more cells in a 10-layer stack may be split into four additional 10-layer stacks, and cultured according to the invention to generation more than $1 \times 10^9$ cells.

The cells may then be shipped directly to the point of treatment location, either fresh or cryopreserved, or may be cryopreserved, stored, and shipped at a later date. Preferably, the cells will be suspended in 10-20 mL (this value is also variable depending on the cell population at harvest, typically can be 10-20 mL) of freezing medium (as described below), and transferred to freezing vials, 1.2 mL of suspension per vial. Each vial will thus contain about $2.2 \times 10^7$ cells, sufficient for injection or other administration into a patient. Cryopreserved cells may be shipped frozen, or may be thawed, washed, and resuspended in appropriate media prior to shipping.

Numerous methods for successfully freezing cells for later use are known in the art and are included in the present invention. The frozen storage of early rather than late passage fibroblasts is preferred because the number of passages in cell culture of normal human fibroblasts is limited.

The method of the invention as described in the above embodiment results in cells which have only been passaged only once or twice.

1.2 mL of fresh (or thawed previously frozen) suspension may be reseeded into a new large flask, or a 5- or 10-layer culture stack if more cells are needed, or a stock of cells for the intended patient are to be maintained, and the above procedure is followed until harvest of the stack. In this embodiment, the resulting stock of cells have been passaged three times.

As used herein, "minimally-passaged" fibroblasts refers to fibroblasts that have been passaged a smaller number of passages in comparison to prior methods. For example, in generating $3 \times 10^8$ or more cells in a single 10-layer stack, the cells have been passaged no more than three times. In embodiments in which the cells have been further cultured into additional 10-layer stacks, the cells may have undergone additional passages, such as up to 4, 5, or 6 passages in generating $1 \times 10^9$ or more cells.

The harvested minimally-passaged fibroblasts may be frozen in any freezing medium suitable for preserving fibroblasts. In one embodiment, freezing medium comprises by volume about 70% growth medium, about 20% FBS and about 10% dimethylsulfoxide (DMSO); however, variations in the composition and proportions in the freezing media will be appreciated by those of skill in the art. However, in a preferred embodiment, no FBS is used in the freezing medium. Preferably the freezing medium comprises, by volume, 50% IMDM, 42.5% cryopreservation solution such as ProFreeze™, and 7.5% DMSO. DMSO may also be substituted with, for example, glycerol. Thawed cells can also be used to initiate new cultures by following the methods of the invention as described above, directly seeding in a 10-layer culture stack, without the inconvenience of obtaining a second specimen.

Any tissue culture technique that is suitable for the propagation of dermal fibroblasts from biopsy specimens may be used to expand the cells to practice the invention as described above, maintaining a low number of passages. Techniques well known to those skilled in the art can be found in R. I. Freshney, Ed., Animal Cell Culture: A Practical Approach (IRL Press, Oxford, England, 1986) and R. I. Freshney, Ed., Culture Of Animal Cells: A Manual Of Basic Techniques, Alan R. Liss & Co., New York, 1987), which are hereby incorporated by reference.

The medium can be any medium suited for the growth of primary fibroblast cultures. The medium can be supplemented with human or non-human serum in an amount of between about 0.0% and about 20% by volume to promote growth of the fibroblasts. Higher concentrations of serum promote faster growth of the fibroblasts. Preferably, growth medium comprises IMDM (containing HEPES and L-glutamine) and 10% fetal bovine serum (FBS). In another embodiment, growth medium comprises glucose DMEM supplemented with about 2 mM glutamine, about 110 mg/L sodium pyruvate, about 10% (v/v) fetal bovine serum and antibiotics, wherein the concentration of glucose ranges from approximately 1,000 mg/L of medium to 4,500 mg/L of medium, and preferably is 4,500 mg/L.

Freshly harvested or thawed cells may be transported at 2-8° C., so long as they are utilized within 72 hours, preferably within 48 hours, and more preferably within 24 hours of their suspension. The cells may be suspended in an appropriate transport medium, a physiological solution with appropriate osmolarity, and may be tested for pyrogens and endotoxin levels. In another embodiment, the cells can be suspended in Krebs-Ringer solution comprising 5% dextrose or any other physiological solution. In a preferred embodiment, the transport medium is DMEM. Cryopreserved cells are preferably transported on dry ice.

The volume of saline or transport medium in which the cells are suspended is related to such factors as the number of fibroblasts the practitioner desires to inject, the extent of the defects to the subject's skin that are to be corrected, the size or number of the defects that are to be corrected, and the urgency of the subject's desire to obtain the results of the treatment. Moreover, the practitioner can suspend the cells in a larger volume of medium and inject correspondingly fewer cells at each injection site.

Preferably, about 10-20 million autologous fibroblasts are administered per administration. Only viable fibroblasts should be administered. Fibroblasts generally remain viable for only about 24 hours outside of culture when stored on ice and thawed. The number of autologous fibroblasts administered in any given administration may need to be adjusted up or down depending upon the potency of the fibroblasts (e.g., collagen production), which may differ with the patient and tissue sources of the fibroblasts and which can be determined in accordance with the assays set forth in Examples 2 and 3 or other assays as are known in the art.

Administrations are repeated as necessary until the desired result is achieved. The timing of a repeat administration, if necessary, is determined by periodic assessment by a physician.

The fibroblasts can be administered with other active agents as desired. For example, the fibroblasts can be administered in conjunction with basic fibroblast growth factor, which stimulates angiogenesis and is mitogenic for growth of keratinocytes and fibroblasts in vivo.

If desired, fetal or juvenile sources of fibroblasts can be used in the context of the present invention. Since fetal cells lack immunogenic determinants, they do not elicit a rejection response to the graft.

The minimally-passaged fibroblasts generated by the method of the invention may be used for the repair, augmentation, or regeneration of a variety of tissues. Many such uses are disclosed in co-owned U.S. Pat. Nos. 5,591,444; 5,858,390; 5,660,850; 5,665,372; 6,432,710; and U.S. Pat. No. 6,878,383, including the repair, augmentation, or regeneration of a variety of tissues. Thus, a pharmaceutical composition of the present invention can be injected into tissues of the subject, and thereby be used to correct defects in the skin, such as scars, wrinkles, laugh lines, rhytids, stretch marks, depressed scars, cutaneous depressions of non-traumatic origin, acne scarring, or subcutaneous atrophy from acne, trauma, congenital malformation, or aging. Moreover, the invention can be used to treat defects such a hypoplasia of the lips, labial folds, vocal cords, or defects in oral mucosa or palate, bone defects, or other connective tissue defects.

In one embodiment, then, the present invention provides a method for regenerating a subject's tissue that (a) has degenerated as a result of a disease or disorder or (b) has a defect, comprising the steps of providing a pharmaceutical composition comprising autologous, minimally-passaged fibroblasts, identifying a site of tissue degeneration, and injecting an effective amount of the composition into tissue at the site of the tissue defect or degeneration so that the tissue is augmented and regeneration of tissue is promoted.

In another embodiment, the method of the invention comprises (a) obtaining a sufficient number of autologous fibroblasts by minimal passaging, and (b) administering the autologous fibroblasts to a defect in skin, bone, or other tissue. The fibroblasts are prepared as a pharmaceutical composition, for direct injection, or may be delivered by other means such as topically. Preferably, the autologous fibroblasts are obtained from a tissue which is the same type of tissue as the defect to be repaired. The fibroblasts are preferably passaged in culture less than three times, more preferably only one or two times. About 10-20 million autologous fibroblasts are preferably administered per treatment.

The present invention provides methods of generating such fibroblasts, and formulating a pharmaceutical composition for the repair, augmentation, or regeneration of tissue, without surgery, wherein the composition is preferably histocompatible with a subject, thereby avoiding elicitation of an immune response and inflammation in the tissues of the subject near the site of degeneration of tissue. The invention also may provide passaged autologous fibroblasts that can withstand resorption so that subsequent injections are not needed, and to prevent the elicitation of an immune response in the subject.

In another embodiment, the present invention provides a method of correcting cosmetic and aesthetic defects in the skin of a subject by the injection of a suspension of autologous dermal fibroblasts into the dermis and subcutaneous tissue subadjacent to the defect. Typical defects that can be corrected by this method include rhytids, stretch marks, depressed scars, cutaneous depressions of non-traumatic origin, scaring from acne vulgaris, and hypoplasia of the lip. Other tissues may also be repaired, such as oral mucosa, the gingival mucosa, or the palatal mucosa, or skin, which has degenerated as a result of a disease or disorder such as periodontal disease, trauma, dermatoses, recurrent aphthous stomatitis, and infections. Additionally, other damaged tissue may be repaired using the fibroblasts generated by the method of the invention, such as burns and burn scars.

The cells that are injected are cells that are preferably histocompatible with the subject, that is, they are autologous cells, that have been expanded by minimal passage in a cell culture system initiated by a biopsy specimen. In a preferred embodiment, the injected cells are dermal fibroblasts drawn from the subject to be treated.

Additionally, in some embodiments, the minimally-passaged fibroblasts may be combined with acellular matrices and/or filler materials, depending on the intended treatment area, as described in the above co-owned patents. Other uses of cultured autologous fibroblasts known in the art are equally amenable to using the minimally-passaged fibroblasts of the invention, such that they reap the benefit of minimal passaging of the fibroblasts.

Conditioned medium stored during the practice of the method of the invention has many uses. For example, it may be used as a topical treatment for a variety of dermal defects, in conjunction with the administration of fibroblasts grown by the method of the invention. Alternatively, the conditioned medium may be formulated into a composition suitable for topical administration without any cells.

EXAMPLES

The following Examples serve to illustrate the present invention and are not intended to limit its scope in any way.

Example 1: Generation of Minimally-Passaged Fibroblasts from Small Biopsy Specimen Initiation of Culture All procedures in this example were performed under sterile conditions. Initially, a dermal fibroblast culture was initiated from a small 1 to 5 mm full thickness biopsy specimen from the skin of a human subject. The biopsy specimen was placed in a 50 mL conical tube and washed three times in a wash medium pre-warmed by incubation at 37.0±2.0° C. for 15 to 30 minutes. The wash media comprised IMDM medium with gentamicin (antibacterial) at a concentration of 30 mg/mL and amphotericin B (antifungal) at a concentration of 15 µg/mL. For each wash, 20 mL of wash medium was added to the 50 mL conical tube, and the biopsy was maintained submerged for 4-6 minutes. The wash media was then removed by pipette.

The washed biopsy specimen was then digested by pipetting 10 ml, of a pre-warmed solution of liberase enzyme for about 60 minutes. The conical tube was then placed in an orbital shaker at 37.0±2.0° C. at 100 rpm for about 120 minutes. The conical tube was then vortexed for 10 seconds.

10 mL of growth medium was pipetted to the tube to neutralize the liberase enzyme and suspend the cells, and the cells were then pelleted in a centrifuge at 150×g for 10 minutes at 5.0±3.0° C. with medium brake and acceleration. Growth medium comprised IMDM (containing HEPES, L-glutamine, antibiotics gentamicin at a concentration of 30 mg/mL and amphotericin B at a concentration of 15 µg/mL), and 10% fetal bovine serum (FBS).

The supernatant was aspirated, and the cells were resuspended in 5.0 mL of growth medium, 40 ml of growth medium was placed in T-225 tissue culture flask and the resuspended cells were then pipetted into the flask. The flask was rocked gently to distribute the cells evenly over the surface. The flask was then incubated at 37.0±2.0° C. with about 4-6% $CO_2$. Supplementation of the flask with 20-50 ml additional pre-warmed growth medium was performed at intervals as needed, about every 3-5 days, and the removed conditioned media was stored for later use.

First Passage to Larger Flask

When the cells reached about 40-100% confluence in the flask, from about 2-3 weeks, they were passaged into a T-500 flask. Generally, reaching this level of confluence requires from about 2 weeks to about 30 days. The passage into a T-500 flask was accomplished by first removing the growth medium, which now comprised a variety of factors secreted from the growing culture (i.e., it was conditioned medium), which was stored for use later. The flask was washed with about 30 mL of phosphate buffered saline (PBS) pipetted into the flask and allowed to rest for 4-6 minutes at room temperature. Then about 5 mL of a solution of trypsin-EDTA (0.05% Trypsin/0.53 mM EDTA) was pipetted to the flask, which was incubated at room temperature for 4-6 minutes to detach the fibroblasts from the wall of the tissue culture flask. When 80-100% of the cells "rounded up", having a round appearance, the sides of the flask were tapped to release the cells into suspension. About 15 mL of pre-warmed growth medium was pipetted to the flask to neutralize the enzyme, and the detached fibroblasts were collected in a 50 mL conical centrifuge tube. An additional 10 mL of growth medium was added to the flask to collect any remaining detached cells, then added to the centrifuge tube. The cells were pelleted, resuspended in 10 mL fresh growth medium, and transferred to an upright T-500 flask pre-filled with 80 mL of pre-warmed growth medium. The resuspended cells were pipetted to the T-500 flask and 10 mL of growth medium was used to rinse the centrifuge tube, which was added to the flask as well. The flask was laid flat to distribute cells and media to all three media layers of the flask. The flask was then incubated at 37.0±2.0° C. with about 4-6% $CO_2$. The T-500 flask was supplemented with additional growth media (about 50 mL as necessary, about every 3-5 days.

Second Passage to 10-Layer Cell Culture Stack

When the cells reached about 95-100% confluence in the T-500 flask, generally in only 3-5 days, they were passaged into a 10-layer culture stack. This was accomplished by first removing the growth medium, (now conditioned medium), which was stored for later use. The flask was washed with about 100 mL of phosphate buffered saline (PBS) pipetted into the flask and allowed to rest for 4-6 minutes at room temperature. Then between about 10-20 mL of a solution of trypsin-EDTA similar to that used previously was pipetted to the flask in an upright position until the layers equilibrated, then the flask was laid flat and gently rocked to ensure the entire growth surface was converged. The flask was then incubated at room temperature for 4-6 minutes to detach the fibroblasts from the wall of the tissue culture flask. When 80-100% of the cells "rounded up", having a round appearance, the sides of the flask were tapped to release the cells into suspension. About 40 mL of pre-warmed growth medium was pipetted to the flask while in the upright position to neutralize the enzyme, and the detached fibroblasts were poured and/or pipetted into a 2 L media bottle pre-filled with 1300 mL of pre-warmed growth media. An additional 50 mL of growth medium was added to the flask to collect any remaining detached cells, then added to the media bottle.

A 10-layer cell culture stack was prepared by replacing one of the standard caps with a universal cap. The contents of the media bottle were then slowly added to the 10-layer culture stack through a sterile funnel in the port, while the opposite standard cap was loosened to vent the stack, swirling the bottle at intervals during the pouring process to ensure capture of as many cells as possible. 100 mL of growth medium was added to the bottle to rinse its surface, and added to the 10-layer culture stack. The universal cap was then replaced with a solid cap. The culture stack was tipped onto the side with the solid cap to allow media to level across all layers of the culture stack, and then tilted towards the end without caps and placed flat again, then gently rocked. Finally, the solid cap was replaced with the original standard cap, and the 10-layer culture stack was incubated at 37.0±2.0° C. with about 4-6% $CO_2$.

Again, fresh growth medium was added to the flask as needed by aspirating about half the volume of media and adding about 750 mL of fresh growth medium in the same manner as described above. The aspirated medium was saved as conditioned medium for later use.

Harvesting of Minimally-Passaged Fibroblasts

When the cells in the 10-layer culture stack reached about 95-100% confluence, they were harvested, yielding about $3.0 \times 10^8$ cells. First, 15 mL of spent growth media was aspirated, to which about $5 \times 10^6$ harvested cells were added, to check for mycoplasma contamination. The remaining spent growth media was aspirated, and saved as conditioned media. 600 mL of PBS was pipetted into the culture stack (300-600 mL may be used for this purpose), replacing its filter vent caps with solid caps, and the culture stack was tipped allowing the PBS to wash all layers of the stack, which was then incubated for 2-3 minutes per wash. The PBS was pipetted or aspirated off after each rinse. 300 mL of Trypsin-EDTA (200-500 mL may be used for this purpose) solution was pipetted into the culture stack and evenly distributed therein. The culture stack was then incubated for 4-6 minutes at 37.0±2.0° C.

When 80-100% of the cells "rounded up", having a round appearance, the sides of the flask were tapped to release the cells into suspension. About 400 mL of pre-warmed growth medium was added and evenly distributed therein to neutralize the enzyme, and the cell suspension was then transferred to two 500 mL conical tubes, about 350 mL in each. 300 mL growth media as used to rinse the culture stack, which was then evenly divided between the two 500 mL conical tubes. The cells were then pelleted in a centrifuge at about 130-170×g for about 10 minutes at 5±3° C. The supernatant was aspirated. 30 mL of growth medium was used to resuspend the cells in one conical tube, then transferred to the other tube. 20 mL of growth medium was then used to rinse the first tube and then added to the other tube. Additional growth medium was then added to the tube containing the cell suspension to bring the total volume to 200 mL. Quality control samples were taken at this time, though they may be taken at any other time during the process.

The cells were then pelleted, the supernatant removed, and the cells resuspended in cold IMDM medium (5±3° C.) to a target concentration of $4.4 \times 10^7$ cells/mL (generally between about 5-10 mL). The cell suspension is then stored in a refrigerator at 5±3° C.

Cryopreservation

In order to cryopreserve the cells, the cell suspension was diluted 1:1 with an equal volume of freeze media comprising 85% ProFreeze™ and 15% DMSO. The volume of freeze media was prepared in a 15 mL tube, and then slowly pipetted dropwise into the cell suspension, allowing the freeze media to run along the side of the tube into the suspension. The tube was then pulse vortexed for 5 seconds, wiped with 70% isopropyl alcohol, then pipetted into cryovials, 1.2 mL or 0.6 mL per vial depending on volume requirements for testing and injection preparation. The suspension was swirled between each vial fill to ensure homogeneous cell suspension during the filling process. Each vial contained about $2.2 \times 10^7$ cells, sufficient for injection or other administration into a patient.

Thawing and Final Preparation

Cells may be shipped fresh, or cryopreserved, or thawed from cryopreservation. To perform a thaw and preparation for two production injection vials, 3.5 vials were warmed to $37.0 \pm 2.0°$ C. until almost completely thawed. The thawed suspension was pipetted into a 50 mL conical tube pre-filled with 17 mL of PBS. Each vial was rinsed with another 1 mL of PBS which was then added to the tube. The cells were then pelleted (150×g for 10 minutes at $5 \pm 3°$ C.). The PBS was aspirated, the cells were resuspended in 17 mL of DMEM, then repelleted. The DMEM wash was aspirated, and then the cells were resuspended in 3.0 mL of DMEM. 0.1 mL of the suspension was removed for quality control analysis. An additional $5 \times 10^6$ cells were collected and added to the previously collected 15 mL of spent media to submit for mycoplasma analysis. The cells were now ready for shipping in a 2-8° C. cold pack system to the practitioner for use. Alternatively, the cells may be shipped cryoperserved, to be thawed at the site where they will be used. After cryofreezing, vials are submitted to quality control for sterility and cell-based testing.

Example 2

Minimally passaged fibroblasts were generated as described in Example 1 above, however, rather than cryopreserving the cells, they were transferred to an additional four 10-layer stacks, and cultured as described above for culturing cells in such stacks. When the cells in the 10-layer culture stacks reached about 95-100% confluence, they were harvested, yielding about $3.0 \times 10^8$ cells per 10-layer stack, thereby producing about $1.2 \times 10^9$ cells. These cells were harvested as described above, ready for cryopreservation or for shipping as fresh cells for treatment of patients.

The present invention is not to be limited in scope by the specific embodiments described above, which are intended as illustrations of aspects of the invention. Functionally equivalent methods and components are within the scope of the invention. Indeed, various modifications of the invention, in addition to those shown and described herein, will become apparent to those skilled in the art from the foregoing description. Such modifications are intended to fall within the scope of the appended claims. All cited references are, hereby, incorporated by reference.

We claim:

1. A topical composition comprising fibroblast conditioned medium, wherein the topical composition is produced by the method comprising the steps of:
    digesting a dermal biopsy specimen obtained from a human and comprising fibroblasts with a dissociative or digestive enzyme to form a fibroblast cell suspension, wherein the dermal biopsy specimen is from 1 to 5 mm in thickness, and between 4 and 12 $cm^2$ in area;
    seeding the fibroblast cell suspension into a first tissue culture flask;
    culturing the fibroblast cell suspension in the first tissue culture flask through at most three passages into a sequentially larger tissue culture flask;
    harvesting the fibroblast conditioned medium from the fibroblast cell suspension during the culturing step, wherein the fibroblast cell suspension comprises $3 \times 10^8$ or more cells at harvest; and
    formulating the conditioned medium into the topical composition.

2. The composition of claim 1, wherein the fibroblast cell suspension is passaged twice.

3. The composition of claim 1, wherein the fibroblast cell suspension is passaged once.

4. The composition of claim 1, wherein the enzyme is a collagenase.

5. The composition of claim 4, wherein the collagenase is liberase.

6. The composition of claim 1, wherein the enzyme is trypsin.

7. The composition of claim 1, wherein the first tissue culture flask is a T-125 flask, T-150 flask, T-175 flask, or T-225 flask.

8. The composition of claim 1, wherein the sequentially larger tissue culture flask is a T-500 flask or multi-layer culture stack.

* * * * *